United States Patent [19]
Lawrence et al.

[11] Patent Number: 5,704,912
[45] Date of Patent: Jan. 6, 1998

[54] SYRINGE ASSEMBLY MOUNTING SYSTEM FOR INFLATION CONTROL SYSTEM

[75] Inventors: Ronald L. Lawrence, San Diego; Jay Sarno, Encinitas, both of Calif.

[73] Assignee: Advanced Cardiovascular Systems, Inc., Santa Clara, Calif.

[21] Appl. No.: 406,040

[22] Filed: Mar. 17, 1995

[51] Int. Cl.$^6$ ............................................ A61M 29/00
[52] U.S. Cl. ................................... 604/97; 604/154
[58] Field of Search ........................ 604/97–99, 151, 604/154, 155, 187; 128/DIG. 1

[56] References Cited

U.S. PATENT DOCUMENTS

| | | | |
|---|---|---|---|
| 4,446,867 | 5/1984 | Laveem et al. | 128/344 |
| 4,624,658 | 11/1986 | Mardorf et al. | 604/121 |
| 4,694,409 | 9/1987 | Lehman | 364/558 |
| 5,209,732 | 5/1993 | Lampropoulos et al. | 604/99 |
| 5,318,534 | 6/1994 | Williams et al. | 604/97 |
| 5,459,700 | 10/1995 | Jacobs | 368/10 |

Primary Examiner—Corrine M. McDermott
Attorney, Agent, or Firm—Fulwider Patton Lee & Utecht, LLP

[57] ABSTRACT

A syringe assembly for an inflation control system having a mounting head at one end is pivotally mounted in a mounting bracket for engagement with a drive arm. The mounting bracket is stationary in relation to the drive arm of the system. The mounting head includes a lateral projection on each of its sides having a shape and size selected for pivotal engagement with notches formed in side walls of the mounting bracket. The handle of the syringe plunger includes a driver retainer for capturing the drive arm in the longitudinal directions so that the longitudinal plunger movement is controlled by the drive arm. Neither the retainer nor the drive arm limits movement in the normal direction so that the syringe can be easily separated from the drive arm by an operator. A clamp secures the syringe barrel in the normal direction. Overcoming the force of the clamp is facilitated by the mechanical advantage provided by the pivotal mounting arrangement of the syringe assembly.

32 Claims, 9 Drawing Sheets

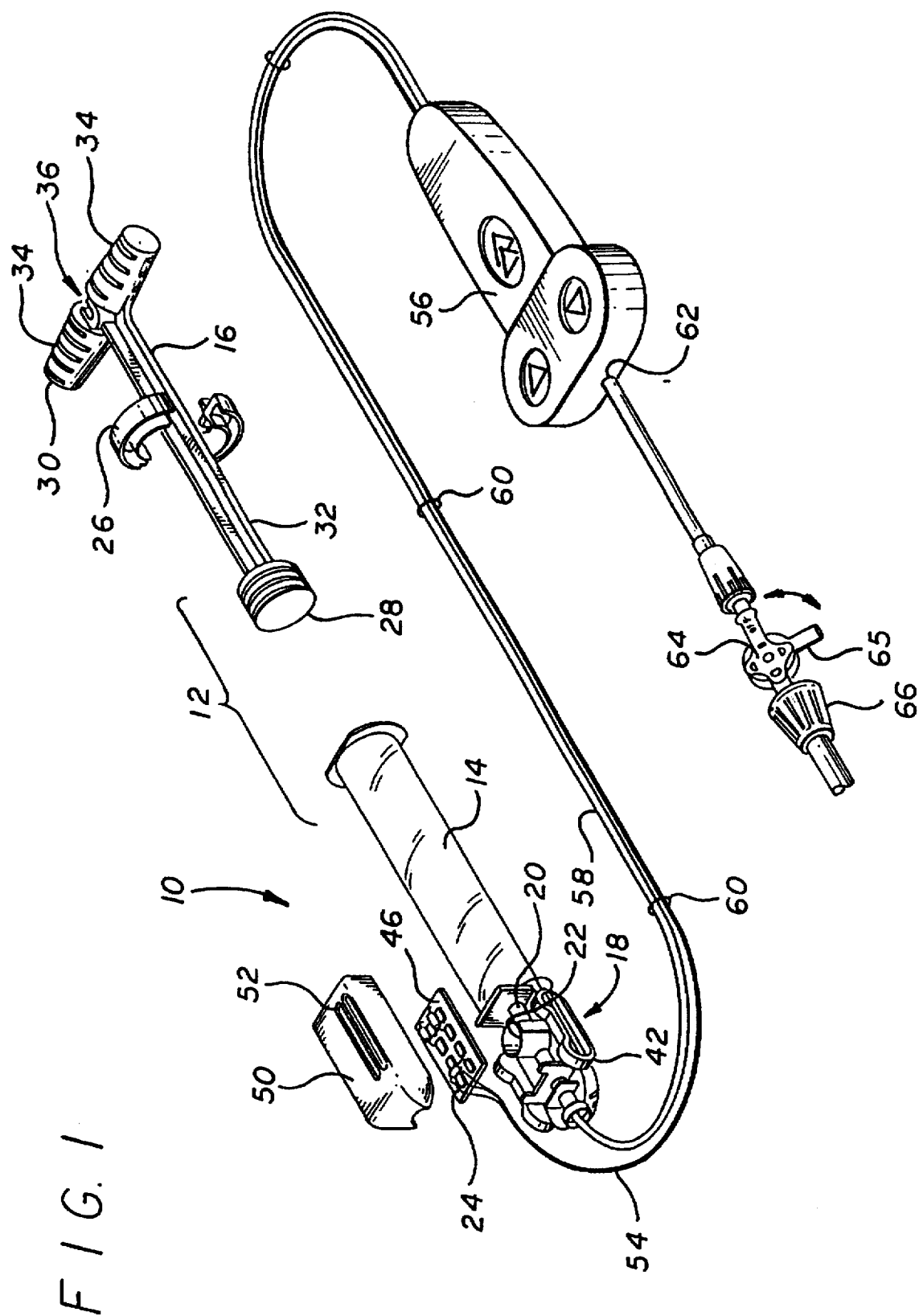

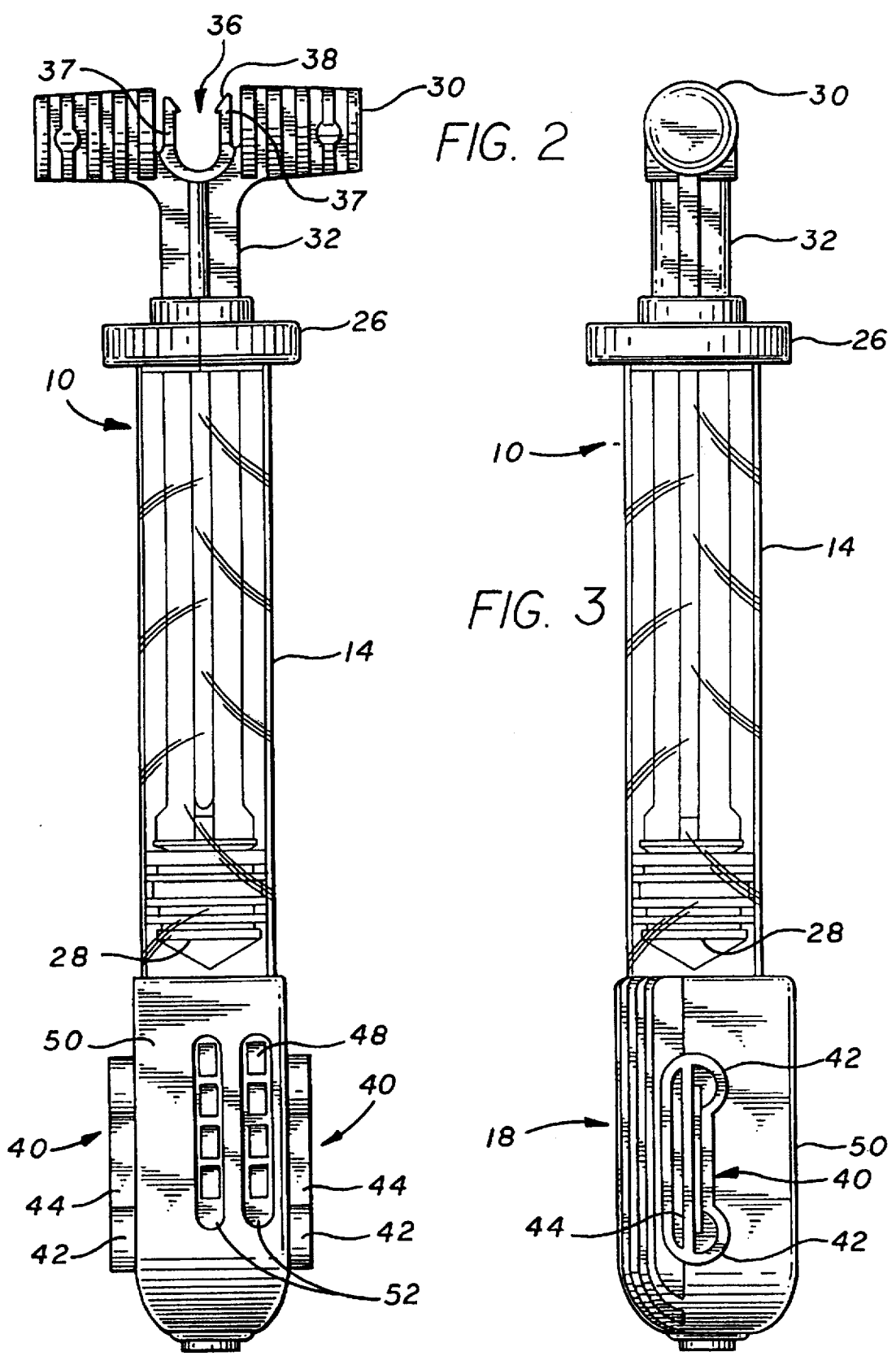

SYRINGE ASSEMBLY MOUNTING SYSTEM FOR INFLATION CONTROL SYSTEM

BACKGROUND

The invention generally relates to inflation devices used in medical procedures, and more particularly, to inflation control systems suitable for controlling the inflation and deflation of balloons or other inflatable devices used in medical procedures, such as balloon catheters used in angioplasty procedures.

Dilatation balloon catheters have been used in increasing numbers in angioplasty procedures to dilate or enlarge blood vessels that have been partially or almost completely blocked by stenosis (a narrowing of the vessel due to injury or disease). Angioplasty procedures have been used to treat stenoses in coronary arteries, peripheral arteries, urethral passages, fallopian tubes, etc. Particularly, the procedure for dilating coronary arteries, referred to as percutaneous transluminal coronary angioplasty (PTCA), has provided an effective and less traumatic treatment technique than coronary by-pass surgery or other surgical treatment methods.

In a typical angioplasty procedure, a guiding catheter is percutaneously introduced into the vascular system of a patient and is directed to a point near the site of the stenosis. Subsequently, a guidewire and a dilatation catheter having an inflatable balloon mounted on the distal end thereof are introduced through the guiding catheter with the guidewire slidably disposed within an inner lumen of the dilatation catheter. The guidewire is advanced out of the distal end of the guiding catheter and is maneuvered into the patient's vasculature containing the stenosis to be dilated, and is then advanced beyond the stenosis. Thereafter, the dilatation catheter is advanced over the guidewire until the dilatation balloon is located across the stenosis. Once in position, the dilatation balloon is inflated to a predetermined size, typically the same size as the inner diameter of the blood vessel at that location, by radiopaque liquid at relatively high pressures (e.g., generally greater than about four atmospheres). The inflated, pressurized balloon radially compresses the atherosclerotic plaque of the stenosis against the inside of the vessel wall to thereby dilate the lumen of the vessel and allow increased blood flow through the vessel.

In a typical PTCA procedure, the balloon is inflated and deflated several times with the pressure maintained for several seconds during each inflation, until the desired patency in the blood vessel is obtained. The physician typically monitors a timing device to control the duration of each inflation and the duration between inflations. Each inflation of the balloon interferes with the blood supply circulation; therefore, the duration must be kept as short as possible, yet must still be long enough to obtain the results desired. The duration between inflations is monitored to allow enough time for the blood supply to reestablish itself before the next inflation. After the procedure has been completed, the balloon is deflated for the final time and maintained under negative pressure so that the dilatation catheter can be withdrawn from the patient and the blood flow resumed through the dilated vessel.

To inflate or deflate the balloon, the physician typically uses an inflation device, such as a syringe, placed in fluid communication with the interior of the balloon. The physician uses one hand to grasp the syringe body and the other hand to maneuver the plunger to pressurize or depressurize the inflation fluid as required. Manually operated syringe-type inflation systems of the type described are manufactured and sold by Advanced Cardiovascular Systems, Inc. of Santa Clara, Calif. under the trademark INDEFLATOR.

Such manual inflation systems have proven to be of great value in conducting angioplasty procedures. Some systems include a pressure sensor with a display that indicates to the operator the fluid pressure in the catheter and balloon. A balloon pressure display allows the physician to monitor whether the arterial plaque causing the stenosis is subjected to a sufficiently high pressure to cause compression of the plaque. Such a display also allows the physician to monitor the pressure to ensure that the balloon pressure limits specified by the manufacturer are not exceeded. Furthermore, if the pressure display indicates a sudden and unexpected decrease in pressure, the physician may be alerted so that any necessary remedial action can be taken.

However, manual systems typically require the physician to use both hands to control the inflation and deflation processes. Each time an adjustment in the location of the balloon in the patient's vessel must be made, the physician must move at least one hand from the inflation control system to the catheter to accomplish the relocation of the balloon, and must then return to the inflation system with both hands. Rather than having to use both hands on the inflation device, it would be preferable for the physician to only use one hand thereby leaving the second hand free to control the position of the catheter in the vessel or to perform other tasks, as needed.

A further consideration with manual inflation systems is the ease with which the system can be used. In manual systems that require a substantial amount of hand strength to maneuver the syringe plunger for developing enough pressure in the balloon to compress the plaque, the physician may experience hand fatigue as a result of operating such an inflation device for several inflation and deflation cycles, each lasting several seconds.

Inflation control systems using a motor drive to control the position of a plunger in a syringe to control the balloon pressure have been described. Such motor drive inflation systems reduce or eliminate the need for the physician to manually control the position of the plunger in the syringe. The physician instead controls the movement of a motor through an electrical switch. That motor performs the work of moving the syringe plunger. Usually only one hand is needed to operate the electrical switch or switches needed for motor control thus leaving one of the physician's hands free to locate the catheter or perform other tasks. Such systems can provide the ability to inflate or deflate the balloon catheter at a precise moment during the maneuvering of the catheter in the patient's vessel with relatively precise control over the rates of inflation and deflation.

Motor driven inflation systems typically use a syringe or syringe-type fluid reservoir for containing the fluid that is to be pressurized to control balloon inflation. Because relatively large pressures can be developed inside the syringe as the balloon is pressurized, it must be securely mounted in relation to the drive mechanism so that the syringe is not prematurely ejected from the drive mechanism. Such ejection could cause an undesired deflation of the balloon in the patient. For example, in the case of a syringe having an elongated plunger, that plunger tends to bend outwardly when a relatively large pressure is developed in the syringe barrel and force continues to be applied to the plunger handle. This bending force tends to make the syringe eject from its mounting structure unless that structure is substantial enough to overcome this force and maintain the syringe in position. However, even though secure mounting of the syringe is needed, the mounting system should not be overly difficult to operate. Preferably, the syringe can be securely mounted to the drive mechanism with a minimum amount of effort and strength required and with relative ease.

Conversely, it is desirable to be able to remove the syringe (or other type of fluid reservoir used to inflate the balloon) from the drive mechanism without delay in the event that the drive mechanism, or other component of the inflation system, ceases to operate properly. For example, motor drive systems typically rely on electrical power as the source of energy for the drive motor. Either batteries or wall power, or both, are used as the power source for the motor. If the electrical power source should become unavailable to the drive mechanism for some reason and the drive mechanism then become unresponsive, the ability to immediately disengage the syringe from the drive mechanism so that it can be operated manually would be desirable. On the other hand, as discussed above, the mounting structure must be sturdy enough to contain the syringe assembly in position as the motor drive controls movement of the plunger and increases and decreases pressures in the syringe barrel.

Another factor of major concern in inflation systems is the cost of the components. In many medical procedures, disposability of the component coming in contact with the patient is required. Re-sterilization of inflation products is in many cases not an option. In other cases, the cost of re-sterilization is cost prohibitive compared to the cost of the item itself. However, the costs must be kept low so that disposability is an option. In the past, disposable manual systems have been relatively costly because of the large number of features included in each system. For example, the incorporation of pressure displays, ratcheting mechanisms, release mechanisms, and other devices all increase the cost of the disposable system. It would be preferable in a motor drive inflation system to provide as many components on a reusable part of the system as possible so that cost of the disposable components is reduced.

Hence those skilled in the art have recognized the need for a motor driven inflation system that operates with a syringe assembly that can be easily and rapidly engaged and disengaged with the motor drive system. Additionally, the need has also been recognized for a motor driven inflation system in which costs are reduced by providing fewer components in the disposable syringe assembly. The present invention fulfills these needs and others.

SUMMARY OF THE INVENTION

The invention is directed to a syringe assembly for engagement with a fixed mounting bracket and with a plunger driver device that is movable in relation to the mounting bracket. The syringe assembly comprises a syringe barrel having a volume and having a first end and a second end, a syringe plunger having a first end movably disposed in the syringe barrel for altering the volume in the syringe barrel and having a second end, a mounting head fixedly disposed at the first end of the syringe barrel, the mounting head having a shape and a size selected for pivotal engagement with the mounting bracket, and a driver retainer disposed at the second end of the syringe plunger adapted to engage the plunger driver device and move therewith.

In a more detailed aspect, the mounting head includes a rounded lateral projection for pivotally engaging the mounting bracket. In further detail, the mounting head includes a second rounded lateral projection for pivotally engaging the mounting bracket, the second rounded lateral projection disposed opposite the first lateral projection. In another aspect, the mounting head has a first lateral side, a second lateral side opposite the first lateral side, and a rounded lateral projection on each lateral side for pivotally engaging the mounting bracket.

In further aspects, the driver retainer includes first and second retainer prongs adapted to receive the driver device between them and snap around the driver device so that the plunger moves with the driver device. The first and second prongs each includes a barb for engaging the rear of the driver device.

In yet another aspect, the plunger comprises a handle disposed at the second end, the handle forming a "T" shape with the plunger. The handle comprises two extensions forming the shape of the T and the driver retainer is located between the two extensions and on the longitudinal axis of the plunger. In a more detailed aspect, the handle comprises two extensions forming the shape of the T and each of the extensions is rounded.

In yet a further aspect, the syringe assembly further comprises a syringe insertion device that is used to indicate the presence of the syringe assembly. The syringe insertion device is disposed in the mounting head and is adapted to interact with a syringe insertion detector when properly mounted into the mounting bracket to indicate the presence of the syringe assembly.

These and other advantages of the invention will become more apparent from the following detailed description thereof when taken in conjunction with the accompanying exemplary drawings.

BRIEF DESCRIPTION OF THE DRAWINGS

FIG. 1 is a partially exploded view of a syringe assembly having a syringe, fluid tubing, and a pressure sensor mounted to the fluid tubing to sense the fluid pressure in that tubing, in accordance with the principles of the invention;

FIG. 2 is a top view of the syringe and pressure sensor of the syringe assembly of FIG. 1 showing the assembled syringe and electrical contacts for the sensor;

FIG. 3 is a side view of the syringe and pressure sensor of FIG. 1;

DETAILED DESCRIPTION OF THE PREFERRED EMBODIMENTS

Figure 4:
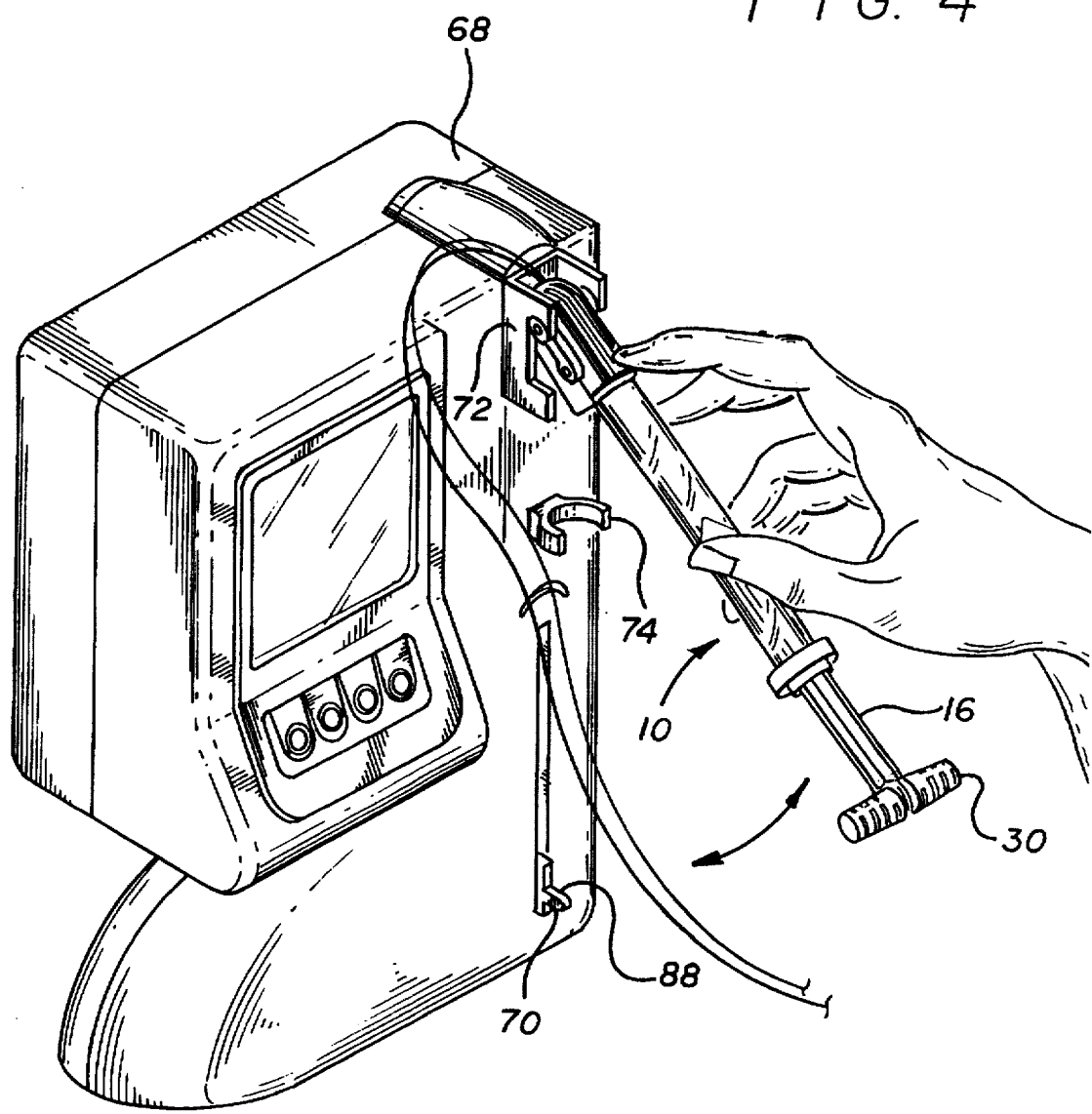
FIG. 4 is a diagrammatic view of the syringe assembly of FIG. 1 being installed into a mounting bracket, and also showing a plunger drive arm.

Referring now to the drawings in which like reference numerals designate like or corresponding features among the several views. FIGS. 1 through 3 illustrate a syringe assembly 10 in accordance with one embodiment of the present invention. The syringe assembly 10 includes a syringe 12 having a syringe barrel 14 and a plunger 16 disposed at one end of the syringe barrel 14 for altering the volume in the syringe barrel depending on its position in the barrel. The syringe assembly also includes a mounting head 18 disposed at the opposite or distal end of the syringe barrel 14 from the plunger 16. Rigid fluid tubing 20 is coupled to the distal opening in the barrel for conducting inflation fluid to and from the syringe barrel. The tubing 20 provides fluid communication with a downstream flexible tubing or fluid line made of any suitable material that can withstand the pressures associated with the inflation and deflation of a balloon catheter or the device on which it is used. The preferred material suitable for the flexible tubing is polyurethane with a braided nylon. Other possible materials are PVC or flexible copolymers.

A sensor port 22 and a pressure sensor 24 are mounted to the fluid tubing 20. The sensor port is in fluid communication with the fluid tubing and therefore the pressure sensor provides an indication of the fluid pressure in the fluid tubing 20. The pressure sensor 24 can be a strain beam type sensor or a piezo-resistive transducer or other types.

The plunger 16 includes a plunger retainer 26 that maintains the plunger at a selected orientation within the syringe barrel 14. The plunger further includes a movable piston 28 that controls the size of the volume in the syringe barrel 14. Moving the piston distally decreases the volume in the syringe barrel and in a closed system, increases the pressure. Moving the piston proximally increases the volume in the syringe barrel and decreases the pressure in a closed system. A plunger handle 30 is connected to the piston through the plunger shaft 32. Movement of the handle causes respective movement of the piston in the barrel.

The plunger handle 30 includes two generally rounded lateral extensions 34 extending in opposite directions from the plunger shaft 32 to form a "T" shape. As will be described in more detail below, the rounded shape of these extensions facilitates grasping the handle by an operator to disengage the syringe assembly from the mounting and driving system for manual control.

A driver retainer 36 is located between the two extensions 34 of the handle 30 and is aligned with the longitudinal axis of the shaft 32. The driver retainer 36 includes two parallel prongs 37 extending in the proximal direction, each prong having a barb 38 disposed at its farthest end on the inside surface. The two parallel prongs of the driver retainer 36 define a space between themselves for accepting and capturing a drive arm for controlling the position of the syringe plunger 16. The operation of the driver retainer 36 will be discussed in greater detail below.

The mounting head 18 is fixedly mounted to the distal end of the syringe barrel 14 and includes a pair of rounded projections 40 located laterally on either side in respect to the syringe barrel 14. These projections 40 are shaped and sized to provide pivotal mounting for the syringe assembly in a mounting bracket as is shown and described in greater detail below. Each projection 40 as shown comprises two rounded ends 42 or ears with a connecting ridge 44 between them. As will be described, the pivotal mounting arrangement with the pivot point being located at one end of the syringe assembly and the point of force for removing the assembly being applied at the other end of the assembly provides greater mechanical advantage to one attempting to remove the syringe assembly 10 from the mounting structure.

While the drawings show that the mounting head 18 and rounded mounting projections 40 are formed separate and apart from the syringe barrel 14, the present invention is not so limited. Other configurations are possible. For example, the rounded projections may simply comprise cylindrical shaped projections, one on either side of the mounting head. Similarly, the mounting head itself may be a part of the syringe barrel in the case where, for example, the pressure sensor is located downstream at a different position.

The mounting head 18 includes a circuit board 46 having open contact surfaces 48 for establishing an electrical connection between circuits in an instrument and circuits in the syringe assembly 10. One circuit in the syringe assembly is the pressure sensor 24 and in this embodiment, the pressure sensor comprises a strain beam type or piezo-resistive type sensor. The circuit board 46 has eight contact surfaces 48 although more or fewer may be required depending on the circuits contained in the syringe assembly 10. In this case, the syringe assembly includes the pressure sensor 24 and the electrical leads for a remote controller 56. A cover 50 protects the board 46 from damage. The cover 50 includes two slots 52 to permit access to the contact surfaces 48 of the circuit board 46.

The circuit board 46 includes lead wires 54 that form an electrical connection with the remote controller 56. The rigid fluid line 20 is in fluid communication with a flexible fluid line 58 that also leads to the remote controller 56 in FIG. 1. The lead wires 54 and flexible fluid line 58 are kept bundled together by a plurality of elastic bands 60. The electrical lead wires 54 terminate in the remote controller 56 while the fluid line 58 travels beyond the remote controller for eventual connection to a catheter (shown in FIG. 8). A slot 62 is formed in the bottom surface of the remote controller 56 along its length and the flexible fluid line 58 is mounted in that slot. The slot 62 is slightly smaller than the flexible tubing 58 and is deep enough so that once inserted, the flexible tubing tends to remain in the slot. This and the banding of the electrical lead wires with the flexible tubing have the advantageous effect of reducing the clutter by retaining the devices together.

Figure 8:
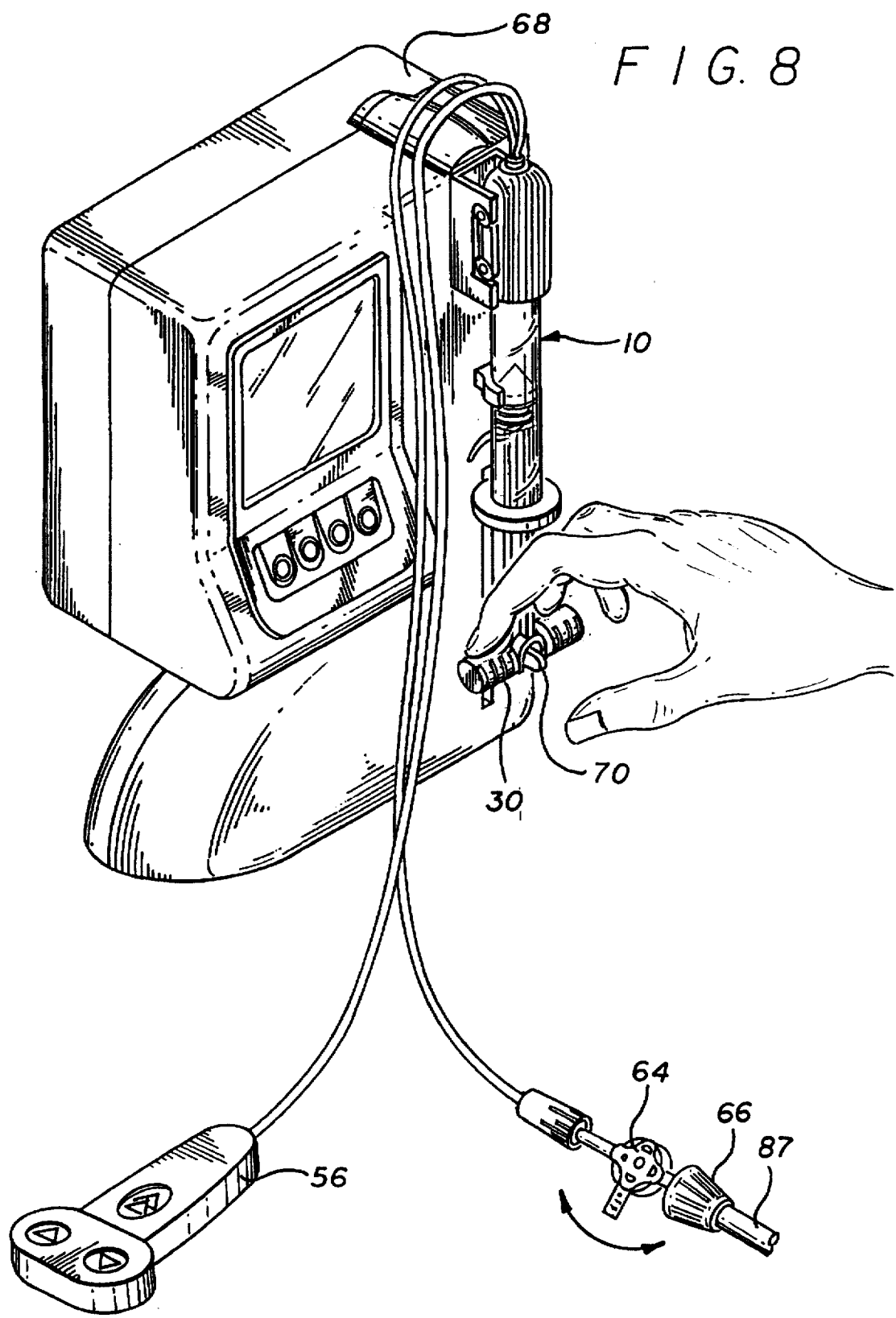
FIG. 8 shows the syringe assembly of FIG. 1 installed in the mounting bracket and clamp on the instrument and a means for rapidly removing the assembly from its mounted position.

The remote controller 56 can be operated either by the physician who also is maneuvering the proximal end of the balloon catheter or may be handled by an assistant standing near the physician but who is not interfering with the physician's handling of the catheter. The assistant would depress the appropriate switch in response to the physician's instructions. In this case, the flexible tubing 58 would be pulled out of the slot 62 to separate it from the controller and the bands 60 moved toward the mounting head 18 so that the controller 56 can be operated by the assistant while the catheter can be operated by the physician. This separated configuration is shown in FIG. 8.

A stopcock device 64 is located at the distal end of the flexible fluid line 58 and a rotating luer lock connector 66 is mounted to the fluid line at a point distal to the stopcock. The stopcock controls the fluid communication of the fluid line 58. Three positions are available in this case. The first position, as shown in FIG. 1, closes the fluid line so no fluid communication with any external device or line can occur. The second position vents the fluid line 58 to outside air, and the third position connects the fluid line to the luer connector 66. In the case where a catheter is connected to the luer connector 66, and the stopcock is placed in the third position, fluid communication now occurs between the fluid line and the catheter. The syringe assembly 10 then controls the pressure in the catheter. Stopcocks and luer connectors are well known to those skilled in the art and no further details are presented here.

Referring now to FIG. 4, the use of the mounting head 18 of the syringe assembly 10 of FIGS. 1 through 3 is shown. In FIG. 4, the syringe assembly 10 is being installed and mounted to an instrument 68. The instrument includes a syringe plunger drive apparatus (not shown) that has a drive arm 70 shown. The drive apparatus may be any of the well known types including a motorized lead screw using a DC motor. The drive apparatus may also be in the form of a DC servo motor, a step motor, a hydraulic motor, a pneumatic motor, or others. Whatever the specific type, the drive apparatus typically includes a moveable drive arm 70 that is capable of directing the movement of another element, such as by pushing or pulling, that it may come in contact with. The drive arm 70 would be connected to the plunger 16 of the syringe 12, which is preferably mounted in a vertical orientation. Other suitable means that can pressurize or depressurize and direct a quantity of fluid may also be used.

The front of the instrument 68 in this case includes a mounting bracket 72 and a clamp 74 for holding the syringe assembly stationary in relation to the drive arm 70. In this case, the clamp 74 is an open C-type clamp with resilient arms that separate upon forcing the syringe barrel 14 through the opening between them and then reclose around the syringe barrel to capture it in place. The C-clamp 74 secures the syringe assembly 10 in position and opposes any force that may be developed by the drive arm 70 that may cause the syringe to eject from its mounting at the front of the instrument. The bracket 72 secures the syringe assembly from movement in the longitudinal, lateral, and rotational directions while the C-clamp secures the syringe assembly from movement in the normal direction. FIG. 4 shows the pivoting motion used to mount the syringe assembly 10 to the instrument 68. The mounting head 18 is first engaged with the mounting bracket 72 and the barrel 14 of the syringe is then placed into the C-clamp 74. As the mounting head 18 is placed into the bracket 72 and the syringe is pivoted into contact with the C-clamp 74, the spring-loaded electrical pins 86 come into contact with respective contact surfaces 48 on the circuit board 46.

Figure 5:
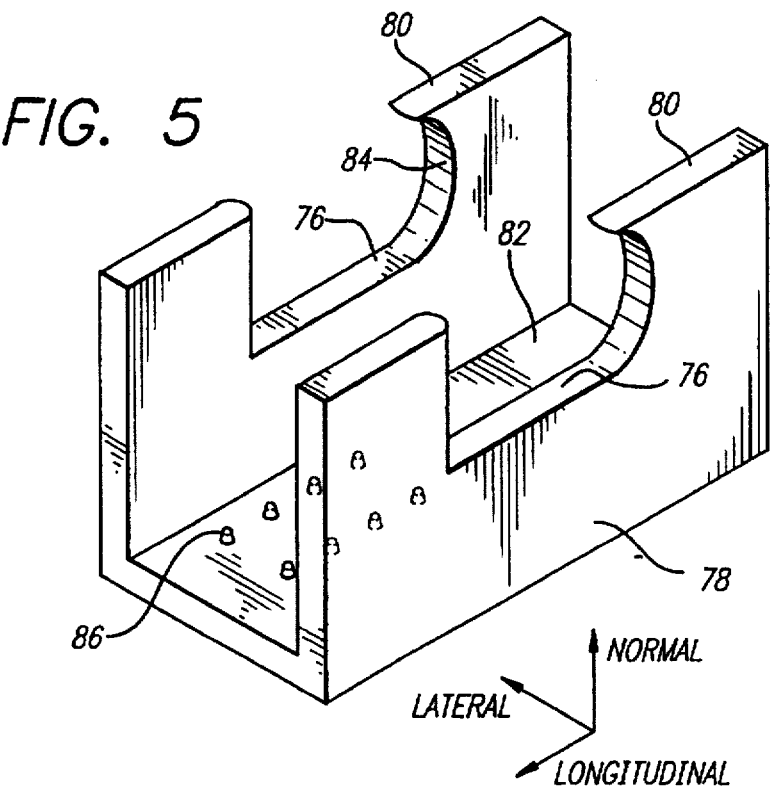
FIG. 5 is a perspective view of the mounting bracket shown in FIG. 4 for receiving the syringe assembly and showing electrical connectors for mating with the pressure sensor.
Figure 6:
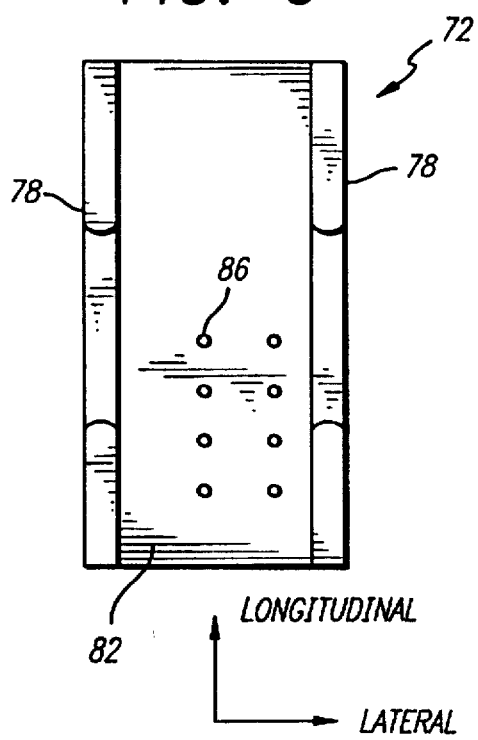
FIG. 6 is a top view of the mounting bracket of FIG. 6.
Figure 7:
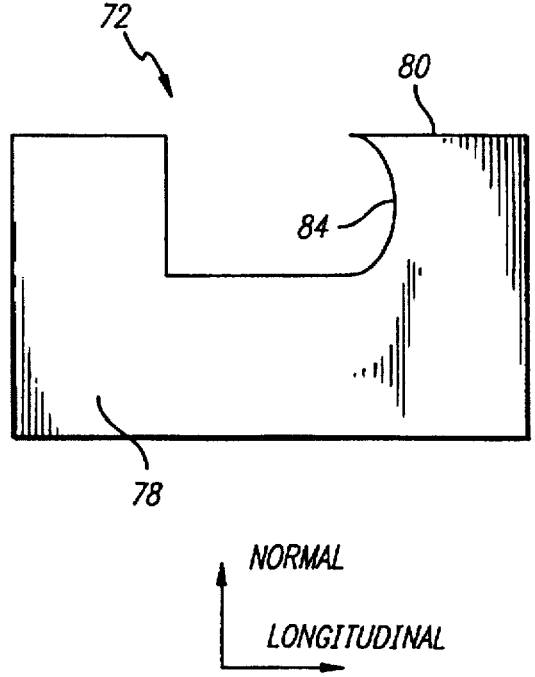
FIG. 7 is a side view of the mounting bracket of FIG. 6.

Referring now to FIGS. 5 through 7 as well as FIG. 4, various views of the mounting bracket 72 are shown. The mounting bracket 72 provides a pivotal connection with the mounting head 18 of the syringe assembly 10. The forward ends of the rounded projections 42 of the mounting head 18 interact with notches 76 formed in respective sidewalls 78 of the mounting bracket 72. The notches are rounded at their distal ends for receiving the rounded projections 42 to facilitate the pivotal connection. The use of a pivotal connection at one end of the syringe assembly with the plunger handle at the other end results in the ability to develop greater mechanical leverage over the syringe assembly for more easily removing it from the instrument 68.

The sidewalls 78 of the bracket 72 limit lateral movement of the syringe assembly 10 while the notch 84 limits movement in a longitudinal direction and limits rotational movement of the syringe assembly. Additionally, the curvature of the front end of the notch assists in limiting movement of the syringe assembly in the normal direction as does the C-clamp. Because the mounting projections 40 must be slid under the top portion 80 of the notch, the notch is made somewhat longer in the longitudinal direction. This length has the advantage or making insertion of the syringe assembly in the bracket easier. Because of the length of the slot, a lower angle of attack may be used in inserting the syringe assembly. In the embodiment shown, it was found that the syringe assembly can be mounted onto the instrument in an average time of two seconds.

FIG. 5 shows a perspective view of the mounting bracket 72 along with a guide illustrating the three coordinate axes in the longitudinal, lateral and normal directions. The base 82 of the mounting bracket 72 resides along a plane defined by the lateral and longitudinal axes. Parallel side walls 78 extend normally from the lateral sides of the base 82. The side walls 78 limit any lateral movement of the mounting head 18 and the syringe assembly 10. The forward longitudinal end of the notch 76 is concave to provide a pivoting surface 84 for mating with the rounded parts 42 of the projections 40 of the mounting head 18.

The plurality of electrical contacts 86 found on the base 82 are in this embodiment spring-biased electrical pins 86 that form a connection with the electrical contacts 48 of the circuit board 46 on a properly installed syringe assembly. As noted earlier, other means of contact engagement with the circuit board can be used and will be apparent to those skilled in the art. The mechanical action of the spring-biased pins 86 permits the mounting action to occur to obtain a proper mounting of the syringe assembly to the instrument while at the same time assuring electrical continuity with the circuit board 46. This technique for providing electrical contacts with the syringe assembly also acts as a security measure in that only a properly mounted syringe assembly will make electrical contact. In one embodiment, an additional means is used to verify the correct mounting of a syringe assembly. A circuit in the instrument monitors for current flow through the circuit board 46. If current flow exists, the presence of a properly installed syringe assembly is concluded. The processor of the instrument monitors this circuit and prevents activation of certain features of the instrument until a syringe has been properly mounted.

Additionally, the locations of the contact surfaces 48 and pins 86 are off center from the longitudinal center line of the syringe assembly as can be clearly seen in FIG. 2. This also assists in assuring that the syringe assembly is mounted properly in that the pins will not contact the pressure sensor surfaces 48 unless the syringe is properly mounted.

Other techniques for determining if the syringe assembly has been correctly mounted may become apparent to those skilled in the art. For example, an optical system may be used that senses the presence of a tag on the syringe assembly. In another embodiment, the position of one or more of the spring-loaded pins may be monitored and when the pin or pins are moved to compress a spring, the presence of a syringe is indicated.

FIG. 8 shows a syringe assembly 10 properly installed on the instrument 68 and connected to an angioplasty catheter 87. The rounded T-shaped handle 30 permits the syringe assembly to be easily grasped when the need arises for removal of the syringe assembly from the instrument. As mentioned above, the pivotal mounting technique provides increased mechanical advantage in pulling the syringe barrel from the C-clamp. This facilitates the rapid and easy removal of the syringe assembly 10 from the instrument 68 should the need arise.

Furthermore, as shown in FIG. 8, the syringe barrel and plunger are mounted vertically with the output of the syringe at the top. Air bubbles will rise to the top of the barrel and will be more apparent as well as easier to eliminate. Once they are at the top of the barrel, moving the plunger in the distal direction will cause them to enter the fluid line 58 where they can be purged.

Figure 9:
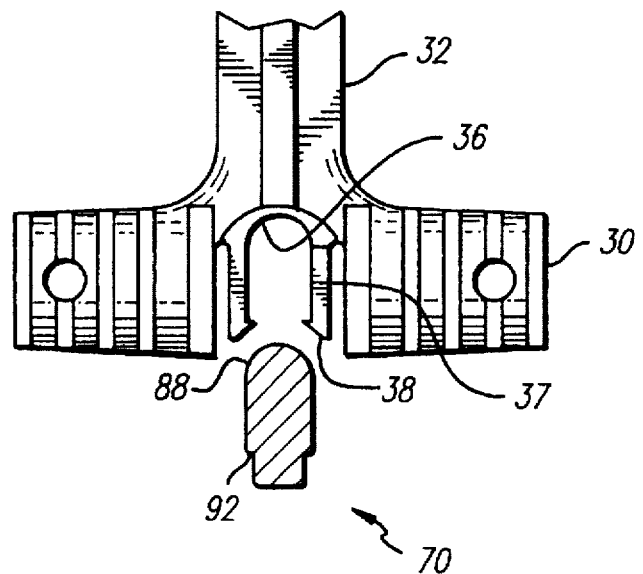
FIGS. 9, 10 and 11 are top views illustrating the sequence in which the drive arm of the syringe plunger driver apparatus engages the driver retainer of the syringe assembly in accordance with the principles of the invention.
Figure 10:
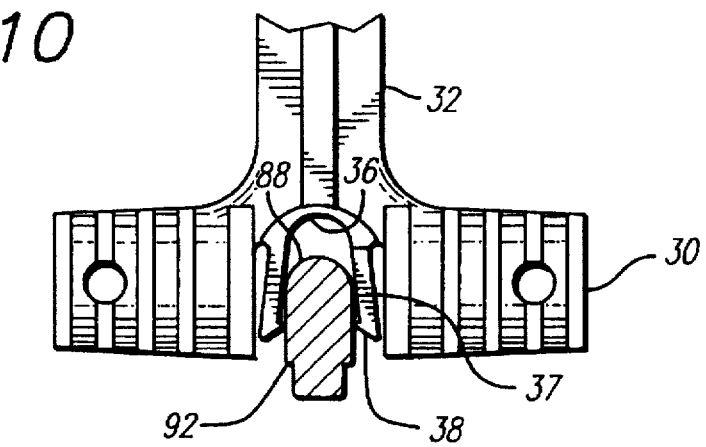
Figure 11:
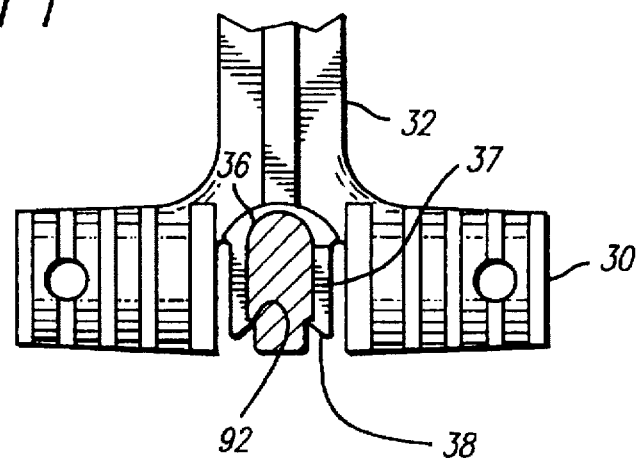

Referring now to FIGS. 9 through 11, the longitudinal receipt and capture of the drive arm by the drive arm retainer 36 of the syringe plunger handle 30 is illustrated. In FIG. 9, the drive arm 70 is moving forward along the longitudinal axis until it touches the barbs 38 of the prongs 37 of the retainer 36. In FIG. 10, the drive arm 70 has continued its longitudinal movement forcing the prongs and barbs apart to allow the drive arm to move between them. Upon moving completely between them as shown in FIG. 11, the prongs and barbs snap back into their at-rest position capturing the drive arm between them. The barbs 38 of the driver retainer 36 have an inward slope that facilitates the movement of the rounded forward face of the drive arm 70 between them. The drive arm has a rounded front surface 88 to assist its movement past the barbs 38. Once the front portion has moved past the barbs, the barbs snap around the drive arm and into notches 92 formed about half way between the rear and front surfaces for accepting the barbs of the retainer 36. The notches 92 of the drive arm 70 should be deep enough so that the barbs will capture the arm and will not allow the arm to pull out of the retainer when the arm is moving in the opposite longitudinal direction.

Additionally, the surfaces of the drive arm are substantially straight and smooth in the normal direction and the surfaces of the plunger retainer are straight and smooth in the normal direction so that the plunger of the syringe can rapidly be slid off the drive arm by pulling it in the normal direction. Thus, the syringe handle can be easily separated from the drive arm in order to facilitate easy removal of the syringe assembly 10. Manually grasping the handle 36 of the syringe assembly 10 enables the operator to manually control the pressure in the system by manually moving the plunger in the syringe. Through this means, the inflated balloon can be easily deflated by the operator manually pulling the plunger in the proximal direction.

Figure 12:
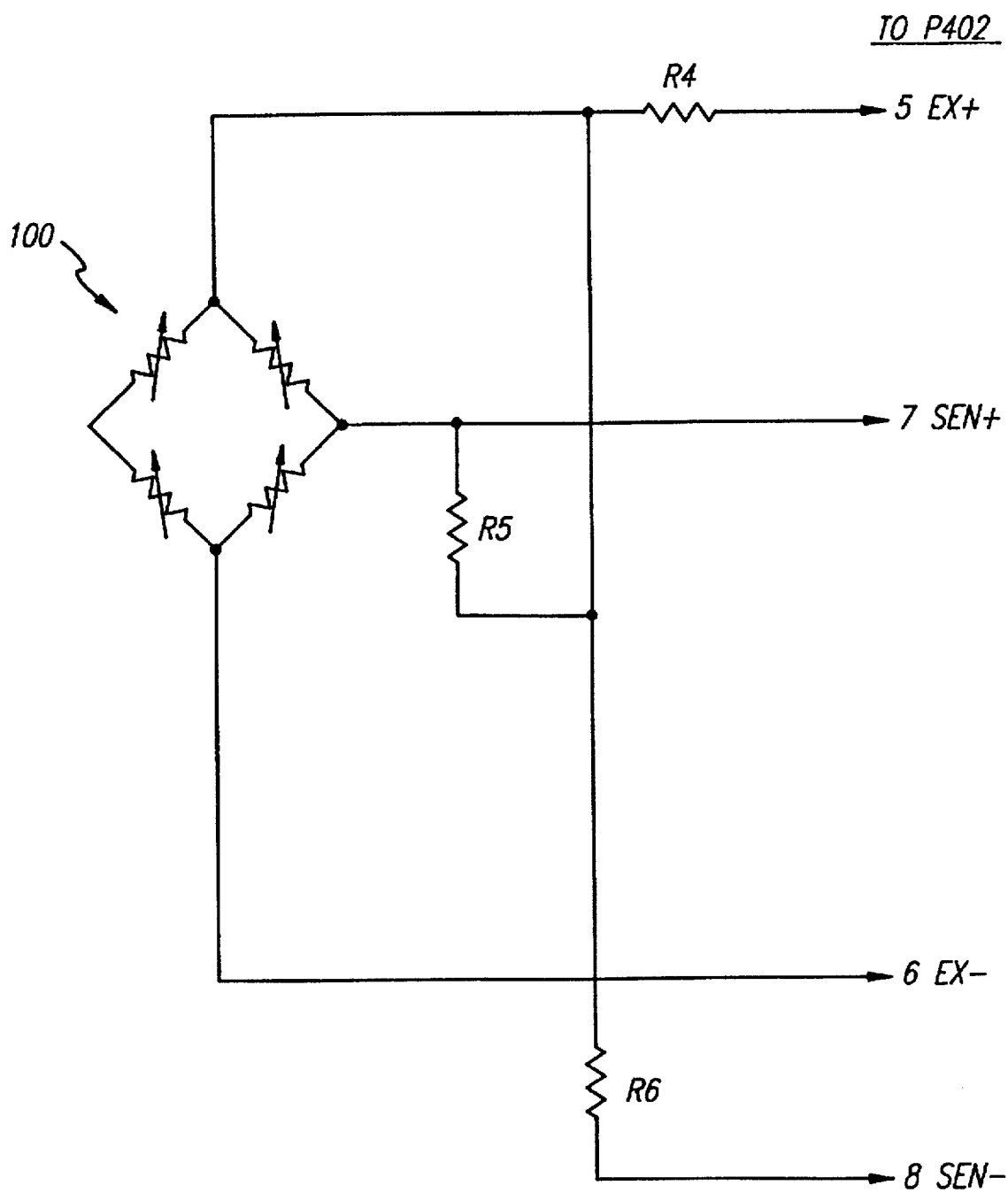
FIG. 12 presents a circuit diagram of a pressure sensor.
Figure 13A:
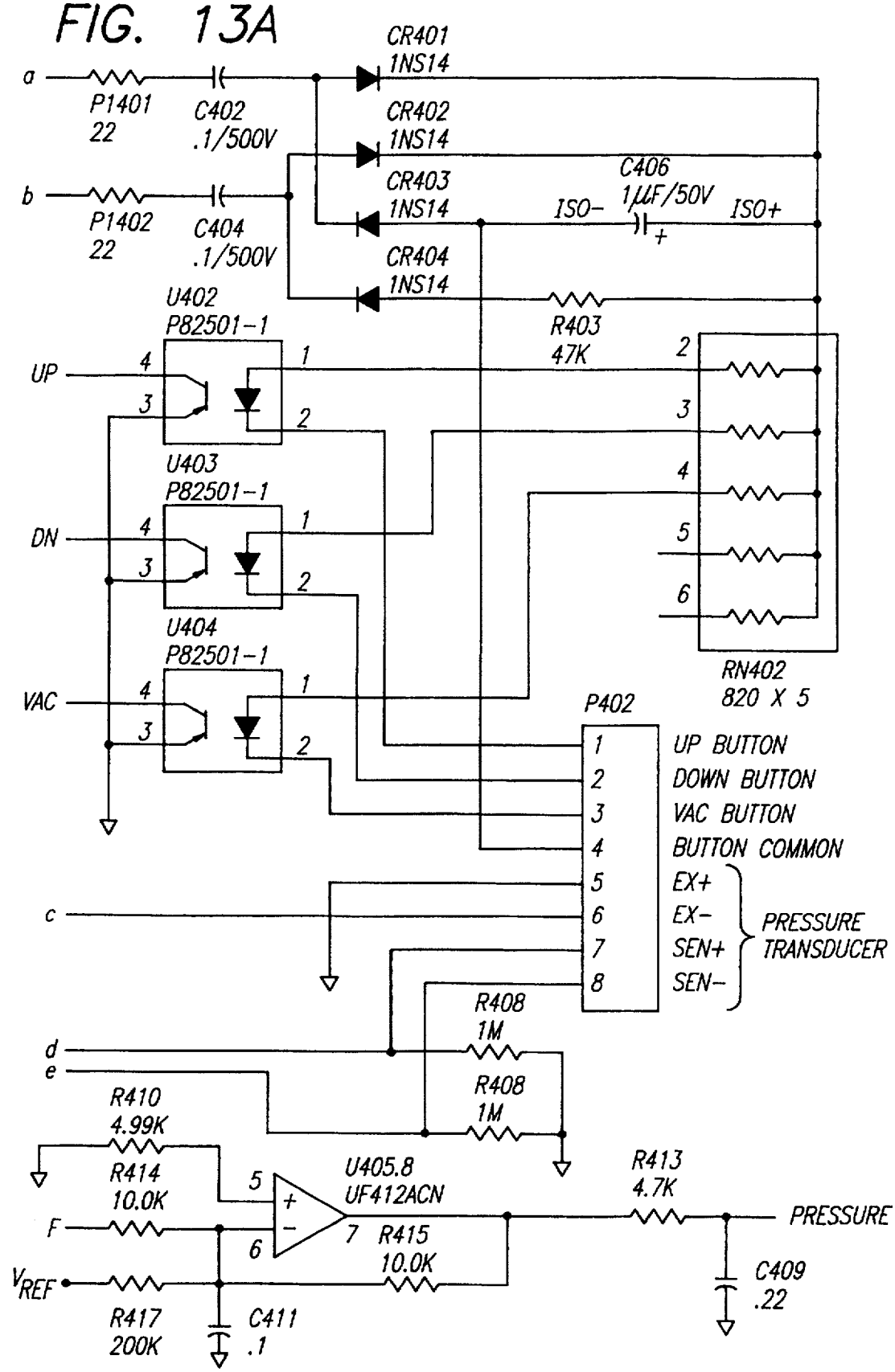
FIGS. 13A and 13B show circuit diagrams of a syringe insertion detector, a floating power source and isolation circuits for the remote controller, and a pressure processing circuit.
Figure 13B:
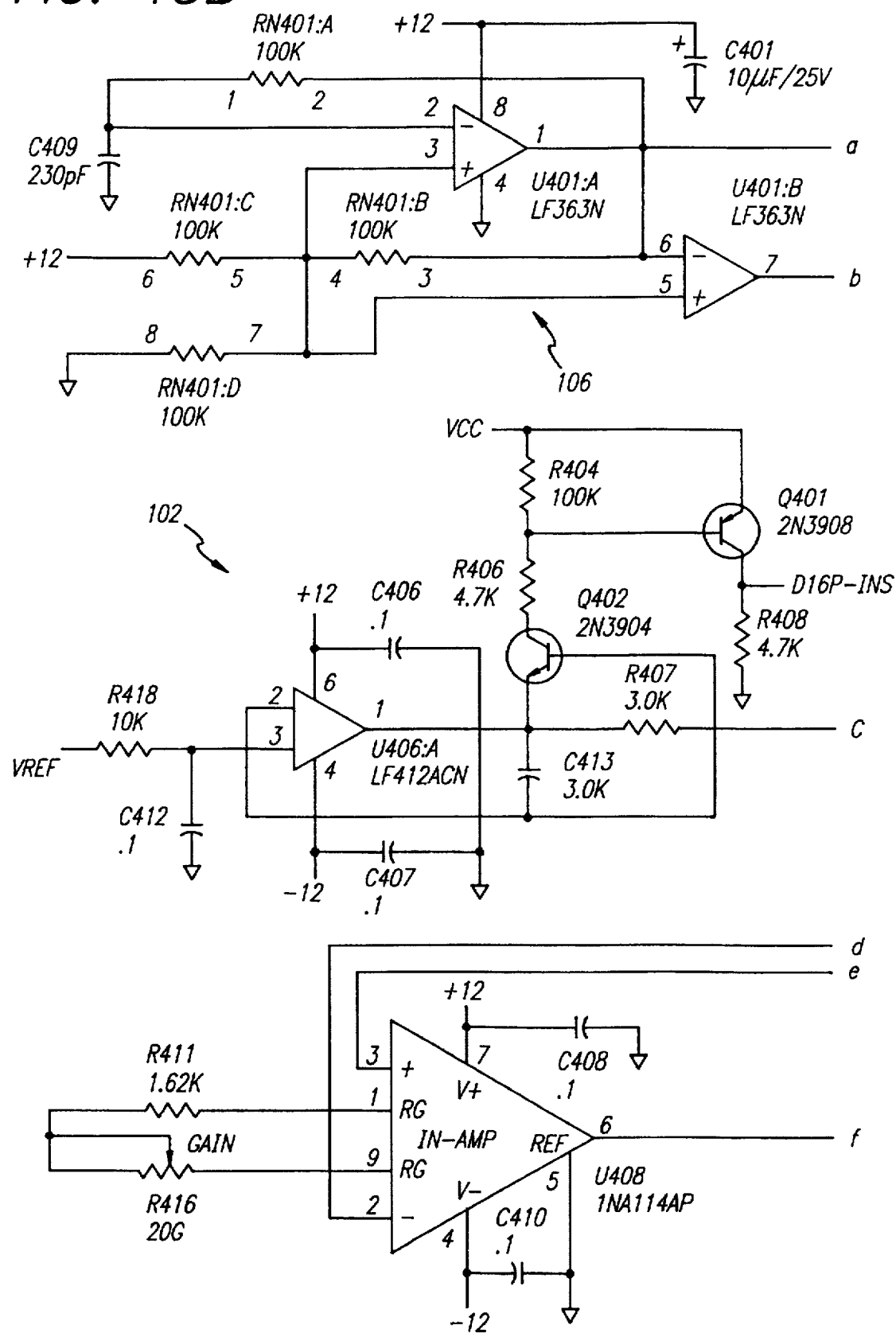

In FIGS. 12, 13A, and 13B, electrical circuit diagrams are presented of a syringe insertion detector. In FIG. 12, a pressure sensing circuit 100 is shown wherein a Wheatstone bridge circuit is used with trim resistors R4, R5, and R6. The operation of this sensing circuit is well known to those skilled in the art. The numbers at the arrowheads indicate pin assignments of the connector P402 shown in FIG. 13 A.

Pin 6 represented as EX- is coupled from connector P402 to a syringe insertion detection circuit 102. When a syringe with the pressure sensor 100 is inserted into the bracket and electrical contact is made with the pins, EX- will have electrical continuity to common through EX+, through the pressure sensor 100. This will turn on transistor Q402, which will turn on transistor Q401 and a signal will be output from DISP-INS indicating the presence of a syringe assembly. The component U405-A provides controlled voltage and transistor Q401 allows the voltage to swing rail to rail. The position detection circuit 102 thus functions by detecting current across the EX+ and EX- lines.

In the above embodiment, the Wheatstone bridge circuit forming a part of the pressure sensor mounted in the syringe assembly functions as a syringe insertion device. Its presence indicates the presence of a properly mounted syringe. Other embodiments are possible, including magnetic devices and optical devices as well as different electrical circuits.

Also shown in FIGS. 13A and 13B is a pressure sensing signal processing circuit 104, the operation of which is apparent to those skilled in the art. An unbalance in the bridge circuit of the pressure sensor 100 causes the levels on the inverting and noninverting inputs of U405 to differ thus causing an output signal. That output signal is provided to U405-B which provides the offset, and a PRESSURE signal results for use by a processor.

Additionally, power and isolation circuits 106 for the switches of the remote controller 56 are shown. Optical isolators U402, U403, and U404 electrically isolate the remote control switch signals from the processor. The UP, DN, and VAC signals are used by a processor to control the movement of a drive arm. The power circuit 106 provides a floating power source for the switches of the controller 56. The floating power circuit 106 isolates the remote controller 56 from ground and from DC sources via capacitors C402 and C404.

The LF353N devices and the LF412ACN devices may be obtained from National Semiconductor. The INA114AP device may be obtained from Burr-Brown, and the PS205-1 devices may be obtained from NEC.

Because the display and drive mechanism are in the instrument and are reusable, the costs of the syringe assembly can be reduced. Other cost reduction features are the use of snap fit collars 26 to secure the plunger in the syringe. Also, the mounting head cover 50 is has a snap fit thereby obviating the need for more expensive adhesive or hardware fastening techniques. The syringe barrel is transparent and is oriented vertically with the output port up so that air bubbles can be easily detected. Because the plunger is lower, the air bubbles may easily be force into the fluid tubing for elimination. The syringe barrel in one embodiment was formed of polycarbonate. The syringe plunger, including the handle, shaft and piston was formed of ABS. The seals on the piston were formed on ethylene propylene diene monomer (EPDM). Other materials may be used.

While specific embodiments of the invention have been described in detail, it will be appreciated by those skilled in the art that various modifications to the structure and use of the disclosed invention may be made in light of the overall teachings of the disclosure, without departing from the scope of the invention as defined by the appended claims.

What is claimed is:

1. A syringe assembly for engagement with a fixed mounting bracket and with a plunger driver device that is movable in relation to the mounting bracket, the syringe assembly comprising:

a syringe barrel having a volume and having a first end and a second end;

a syringe plunger having a first end movably disposed in the syringe barrel for altering the volume in the syringe barrel and having a second end, with a syringe plunger longitudinal axis passing through said first end and said second end;

a mounting head fixedly disposed at the first end of the syringe barrel, the mounting head having a shape and a size selected for pivotal engagement with the mounting bracket, said pivotal engagement allowing the syringe assembly to pivot about a pivot axis which passes through the mounting bracket and which is non-parallel with the syringe plunger longitudinal axis; and a driver retainer disposed at the second end of the syringe plunger adapted to engage the plunger driver device and move therewith.

2. The syringe assembly of claim 1 wherein the mounting head has a first lateral side, a second lateral side opposite the first lateral side, and a rounded lateral projection on each lateral side for pivotally engaging the mounting bracket.

3. The syringe assembly of claim 1 further comprising:

a syringe insertion device disposed on the syringe barrel for indicating the presence of the syringe assembly.

4. The syringe assembly of claim 1 further comprising:
a syringe insertion device disposed in the mounting head for indicating the presence of the syringe assembly.

5. A syringe assembly for engagement with a fixed mounting bracket and with a plunger driver device that is movable in relation to the mounting bracket, the syringe assembly comprising:
a syringe barrel having a volume and having a first end and a second end;
a syringe plunger having a first end movably disposed in the syringe barrel for altering the volume in the syringe barrel and having a second end;
a mounting head fixedly disposed at the first end of the syringe barrel, the mounting head having a shape and a size selected for pivotal engagement with the mounting bracket, wherein the mounting head includes a rounded lateral projection for pivotally engaging the mounting bracket; and
a driver retainer disposed at the second end of the syringe plunger adapted to engage the plunger driver device and move therewith.

6. The syringe assembly of claim 5 wherein the mounting head includes a second rounded lateral projection for pivotally engaging the mounting bracket, the second rounded lateral projection disposed opposite the first lateral projection.

7. A syringe assembly for engagement with a fixed mounting bracket and with a plunger driver device that is movable in relation to the mounting bracket, the syringe assembly comprising:
a syringe barrel having a volume and having a first end and a second end;
a syringe plunger having a first end movably disposed in the syringe barrel for altering the volume in the syringe barrel and having a second end;
a mounting head fixedly disposed at the first end of the syringe barrel, the mounting head having a shape and a size selected for pivotal engagement with the mounting bracket; and
a driver retainer disposed at the second end of the syringe plunger adapted to engage the plunger driver device and move therewith, wherein the drive retainer includes first and second retainer prongs adapted to receive the driver device between them and snap around the driver device so that the plunger moves with the driver device.

8. The syringe assembly of claim 7 wherein the first and second prongs each includes a barb for engaging a rear portion of the driver device.

9. A syringe assembly for engagement with a fixed mounting bracket and with a plunger driver device that is movable in relation to the mounting bracket, the syringe assembly comprising:
a syringe barrel having a volume and having a first end and a second end;
a syringe plunger having a first end movably disposed in the syringe barrel for altering the volume in the syringe barrel and having a second end, wherein the plunger comprises a handle disposed at the second end, the handle forming a "T" shape with the plunger;
a mounting head fixedly disposed at the first end of the syringe barrel, the mounting head having a shape and a size selected for pivotal engagement with the mounting bracket; and
a driver retainer disposed at the second end of the syringe plunger adapted to engage the plunger driver device and move therewith.

10. The syringe assembly of claim 9 wherein:
the handle comprises two extensions forming the shape of the T; and
the driver retainer is located between the two extensions and on the longitudinal axis of the plunger.

11. The syringe assembly of claim 9 wherein:
the handle comprises two extensions forming the shape of the T; and
each of the extensions is rounded.

12. A mounting system for mounting a syringe assembly with a movable driver device, the system comprising:
a mounting bracket located in a stationary position in relation to the moveable driver device;
a syringe barrel having a volume and having a first end and a second end;
a syringe plunger having a first end movably disposed in the syringe barrel for altering the volume in the syringe barrel and having a second end, with a syringe plunger longitudinal axis passing through said first end and said second end;
a mounting head fixedly disposed at the first end of the syringe barrel and received in the mounting bracket, the mounting head having a shape and a size selected for pivotal engagement with the mounting bracket, wherein the syringe assembly can pivot about a pivot axis which passes through the mounting bracket and which is non-parallel with the syringe plunger longitudinal axis; and
a driver retainer disposed at the second end of the syringe plunger adapted to engage the plunger driver device and move therewith.

13. The mounting system of claim 12 wherein:
the bracket includes two notches disposed on opposite sides of the bracket;
the mounting head has a first lateral side, a second lateral side opposite the first lateral side, and a rounded lateral projection on each lateral side for pivotally engaging respective notches of the mounting bracket.

14. The mounting system of claim 12 wherein the syringe assembly further comprises a syringe insertion device disposed on the syringe barrel for indicating the presence of the syringe assembly.

15. The mounting system of claim 14 wherein the syringe insertion device is disposed at the distal end of the syringe barrel.

16. The mounting system of claim 14, further comprising:
a syringe insertion detector that detects the syringe insertion device upon the proper insertion of the syringe assembly into the mounting bracket, said syringe insertion detector generating a signal indicating proper insertion of the syringe assembly into the mounting bracket.

17. The mounting system of claim 12 further comprising:
a detector connected to the mounting bracket that provides a signal indicating proper insertion of the syringe assembly into the mounting bracket.

18. The mounting system of claim 17 wherein the detector comprises an electrical pin that completes an electrical circuit upon proper insertion of the syringe assembly into the mounting bracket.

19. A mounting system for mounting a syringe assembly with a movable driver device, the system comprising:
a mounting bracket located in a stationary position in relation to the moveable driver device, the bracket comprising a notch;

a syringe barrel having a volume and having a first end and a second end;

a syringe plunger having a first end movably disposed in the syringe barrel for altering the volume in the syringe barrel and having a second end;

a mounting head fixedly disposed at the first end of the syringe barrel and received in the mounting bracket, the mounting head having a shape and a size selected for pivotal engagement with the mounting bracket, the mounting head including a rounded lateral projection for pivotally engaging the notch of the mounting bracket; and a driver retainer disposed at the second end of the syringe plunger adapted to engage the plunger driver device and move therewith.

20. The mounting system of claim 19 wherein:

the bracket comprises a second notch disposed opposite the bracket from the first notch;

the mounting head includes a second rounded lateral projection for pivotally engaging the second notch of the mounting bracket, the second rounded lateral projection disposed opposite the first lateral projection on the mounting head.

21. A mounting system for mounting a syringe assembly with a movable driver device, the system comprising:

a mounting bracket located in a stationary position in relation to the moveable driver device;

a syringe barrel having a volume and having a first end and a second end;

a syringe plunger having a first end movably disposed in the syringe barrel for altering the volume in the syringe barrel and having a second end;

a mounting head fixedly disposed at the first end of the syringe barrel and received in the mounting bracket, the mounting head having a shape and a size selected for pivotal engagement with the mounting bracket; and a driver retainer disposed at the second end of the syringe plunger adapted to engage the plunger driver device and move therewith, the driver retainer including first and second retainer prongs adapted to receive the driver device between them and snap around the driver device so that the plunger moves with the driver device.

22. The mounting system of claim 21 wherein the first and second prongs each includes a barb for engaging a rear portion of the driver device.

23. A mounting system for mounting a syringe assembly with a movable driver device, the system comprising:

a mounting bracket located in a stationary position in relation to the moveable driver device;

a syringe barrel having a volume and having a first end and a second end;

a syringe plunger having a first end movably disposed in the syringe barrel for altering the volume in the syringe barrel and having a second end, wherein the plunger comprises a handle disposed at the second end, the handle forming a "T" shape with the plunger;

a mounting head fixedly disposed at the first end of the syringe barrel and received in the mounting bracket, the mounting head having a shape and a size selected for pivotal engagement with the mounting bracket; and a driver retainer disposed at the second end of the syringe plunger adapted to engage the plunger driver device and move therewith.

24. The mounting system of claim 23 wherein:

the handle comprises two extensions forming the shape of the T; and the driver retainer is located between the two extensions and on the longitudinal axis of the plunger.

25. The mounting system of claim 23 wherein:

the handle comprises two extensions forming the shape of the T; and each of the extensions is rounded.

26. A mounting system for mounting a syringe assembly with a movable driver device, the system comprising:

a mounting bracket located in a stationary position in relation to the moveable driver device;

a syringe barrel having a volume and having a first end and a second end;

a syringe plunger having a first end movably disposed in the syringe barrel for altering the volume in the syringe barrel and having a second end;

a mounting head fixedly disposed at the first end of the syringe barrel and received in the mounting bracket, the mounting head having a shape and a size selected for pivotal engagement with the mounting bracket;

a driver retainer disposed at the second end of the syringe plunger adapted to engage the plunger driver device and move therewith;

a plurality of electrical contacts in the mounting bracket;

a plurality of electrical contacts in the syringe assembly positioned to form connections with the mounting bracket electrical contacts when the syringe assembly is properly inserted into the mounting bracket; and an electrical circuit that monitors current flow through the connections formed by the syringe assembly electrical contacts and mounting bracket electrical contacts, said electrical circuit providing a signal indicating proper insertion of the syringe assembly into the mounting bracket.

27. The mounting system of claim 26 wherein the syringe assembly has a longitudinal center line, and the syringe assembly electrical contacts are located off center from said longitudinal center line.

28. A syringe assembly for engagement with a fixed mounting bracket and with a plunger driver device that is movable in relation to the mounting bracket, the syringe assembly comprising:

a syringe barrel having a volume and having a first end and a second end;

a syringe plunger having a first end movably disposed in the syringe barrel for altering the volume in the syringe barrel and having a second end, with a longitudinal axis passing through said first end and said second end;

a mounting head fixedly disposed on the syringe barrel, the mounting head having a shape and a size selected for engagement with the mounting bracket; and a driver retainer disposed at the second end of the syringe plunger adapted to longitudinally receive and capture the plunger driver device and longitudinally move therewith.

29. The syringe assembly of claim 28 wherein the driver retainer longitudinally secures the plunger driver device to the syringe plunger while permitting movement of the syringe plunger away from the plunger driver device in a normal direction.

30. The syringe assembly of claim 28 wherein the driver retainer includes first and second retainer prongs adapted to receive the driver device between them and snap around the driver device so that the plunger moves with the driver device.

31. The syringe assembly of claim 30 wherein the first and second prongs each includes a barb for engaging a rear portion of the driver device.

32. The syringe assembly of claim 28 wherein:

the second end of the syringe plunger comprises a handle having two extensions forming the shape of a T; and the driver retainer is located between the two extensions and on the longitudinal axis of the plunger.

* * * * *